United States Patent [19]

Hansen et al.

[11] 4,284,355

[45] Aug. 18, 1981

[54] AUTOMATED METHOD FOR CELL VOLUME DETERMINATION

[75] Inventors: W. Peter Hansen, Middleboro; Robert A. Hoffman, Mansfield; Peter J. Natale, Canton, all of Mass.

[73] Assignee: Ortho Diagnostics, Inc., Raritan, N.J.

[21] Appl. No.: 89,654

[22] Filed: Oct. 29, 1979

[51] Int. Cl.³ .......................................... G01N 21/17
[52] U.S. Cl. ............................ 356/335; 250/461 B; 356/39; 356/379
[58] Field of Search ................. 356/39, 335, 336, 339, 356/379; 250/458, 461 B

[56] References Cited

U.S. PATENT DOCUMENTS

| 3,275,834 | 9/1966 | Stevens | 356/39 |
|---|---|---|---|
| 3,869,208 | 3/1975 | Lorenz | 356/336 |
| 3,883,247 | 5/1975 | Adams | 356/39 |
| 3,946,239 | 3/1976 | Salzman et al. | 356/39 |

Primary Examiner—R. A. Rosenberger
Attorney, Agent, or Firm—Audley A. Ciamporcero, Jr.

[57] ABSTRACT

Fluorescence volume exclusion signals are utilized to evaluate cell volume. Cells are suspended in a medium which is furnished with a fluorescent dye which neither penetrates nor adheres to the cells. Cells are analyzed by an optical flow cytometer, with illumination which causes the dye medium to fluoresce. Passage of a cell through the sensing zone therefore reduces the amount of fluorescent medium being illuminated, and proportionally reduces the fluorescence output signal. Fluorescence volume exclusion pulse height and area are related to cell volume.

6 Claims, 2 Drawing Figures

AUTOMATED METHOD FOR CELL VOLUME DETERMINATION

FIELD OF THE INVENTION

This invention relates to automated study and characterization of biological materials, and more particularly to automated methods for determining cell volume.

BACKGROUND AND PRIOR ART

In many areas of biology and medicine, it is important to know the volume of a cell. For example, the mean cell volume (MCV) of erythrocytes is a standard hematological parameter used in the diagnosis of disease.

A conventional and rather straightforward method which has been used to determine mean volume of cells in a suspension, such as blood, is to sediment the cells and measure the total volume of the cell suspension and the volume occupied by the packed, sedimented cells. Cell concentration is measured by independent means, and mean cell volume is calculated as the packed cell volume divided by the product of total volume and cell concentration. This method is reasonably accurate, but not sufficiently so for certain high accuracy applications, which require that corrections be made for liquid trapped between the packed cells. Furthermore, the method itself is tedious and lengthy.

It is accordingly a primary object of the present invention to provide automated cell volume determination methods which avoid the need to sediment cells from the suspension, and which further obviate errors occasioned by incomplete sedimentation packing. It is an associated object that the improved methods be brief, simple, and essentially quantitatively repeatable.

The prior art also includes approaches to improvement on the suspension-packing approach to cell volume measurement, by utilizing flow through cell analyzers, also known in the art as flow cytometers. Various types of these approaches are shown in the prior art, including U.S. Pat. No. 3,275,834 to Stevens, and No. 2,565,508 to Coulter. These are intended to improve on the speed and precision with which cell volume measurements can be made.

In flow cytometric instruments, cells in suspension pass through a sensing zone which provides signals related to various cellular properties. Generally, cell concentration is low enough so that only one cell is in the sensing zone at any time. In systems exemplified by the Stevens patent, the sensing zone is defined by a light beam, whereas in systems exemplified by the Coulter patent, the sensing zone is an electrical impedance sensing orifice. When the sensing zone is a light beam, conventional approaches to flow cytometric cell volume typically utilize light scattering or extinction as measures of cell size. These optical signals, however, also depend on cell shape and refractive index, as well as cell volume, thereby introducing potentiality for error. In systems utilizing an electrical impedance sensing orifice as the sensing zone, change in orifice impedance is used as measure of cell volume, and this approach involves inherent error depending upon the shape and the electrical resistance of the cell. Accordingly, present flow cytometric approaches to measurement of cell volume are generally characterized by deficiencies introduced by cellular properties other than volume which simultaneously, are sensed and which are difficult to isolate, evaluate, and thereby correct. For example, utilizing either of the approaches disclosed in the foregoing Coulter or Stevens patents makes it likely that two cells of equal volume but different shape may be erroneously measured as having two different cell volumes.

It is an object of the present invention to utilize flow cytometric apparatus for the automated measurement of cell volume, but in a fashion which eliminates or substantially reduces the dependence of actual cell volume measurement on other cellular properties such as shape, refractive index, and cell impedance.

SUMMARY OF THE INVENTION

The principles of the present invention are grounded on the proposition of utilizing fluorescent volume exclusion in optical flow cytometers. In accordance with the principles of the present invention, cells are suspended in an isotonic medium containing a fluorescent dye, which neither enters into the cells nor attaches to cell surface. The cell suspension is passed through a flow cytometer in which the cell suspension is formed into a cylindrical sample stream which passes through a focused light beam. The sample stream is larger in diameter than the cells, and cells in the sample stream pass individually through the light beam. The wave length of the light which illuminates the sample stream is chosen so that the fluorescent dye in the sample stream is efficiently excited. Fluorescent light from the sample stream is collected by suitable lenses and filters, and applied to a detector such as a photomultiplier tube. In accordance with the principles of the present invention, as in conventional flow cytometric approaches, a sensing zone is defined by the intersection of the sample stream and the focused light beam. In accordance with the present invention, however, when a cell is absent from the sensing zone, the dye in the sample stream produces a steady level of fluorescent light, which, in turn, produces a constant output from the detector. When a cell enters the sensing zone, a volume of fluorescent dye equal to the volume of the cell is excluded from the sensing zone, and the intensity of fluorescent light emitted from the sensing zone is reduced accordingly. This reduction in fluorescent light is registered as a decrease in the output of the detector. When a cell passes through the sensing zone, it produces a pulse whose amplitude is therefore proportional to the volume of the cell.

BEST MODE FOR CARRYING OUT THE INVENTION

Figure 1:
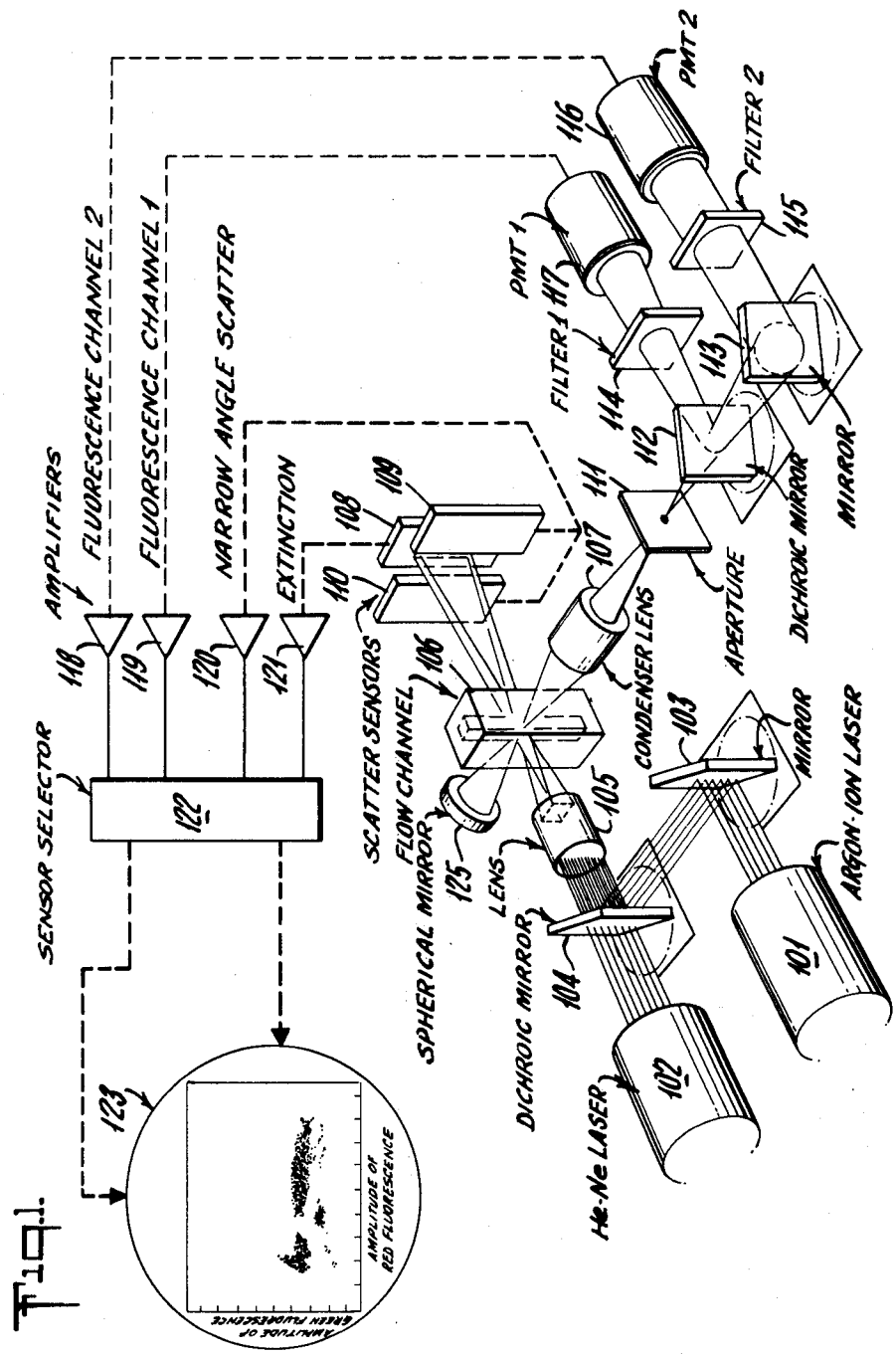
FIG. 1 shows a stylized version of a commercially available flow cytofluorometric apparatus.

Referring first to FIG. 1, there is shown a stylized functional and structural representation of apparatus which may be utilized in accordance with the principles of the present invention. In fact, the apparatus of FIG. 1 depicts a particular system available commercially under the trade designation CYTOFLUOROGRAPH®, which is sold by Ortho Instruments, 410 University Avenue, Westwood, Massachusetts 02090. The apparatus of FIG. 1 incorporates the principles of flow cytometry for cell analysis, and includes capacity for sensing cell fluorescence response to specific types of illumination.

Focal to the FIG. 1 apparatus is a flow channel 106, wherein cells in liquid suspension are passed, in single file and at a rapid rate (e.g. 2500 cells per second) through a sensing zone. The sensing zone is defined by the intersection of cell flow and an incident light beam, typically focused coherent light from a gas laser. As the cell passes through the sensing zone, it interacts with incident light in a variety of ways. Some light, of course, is absorbed by the cell, other light is scattered at relatively narrow angles to the axis of incident light, and still other light is scattered at angles quite divergent from the axis of incident light, for example at right angles to the incident light. Furthermore, depending upon the nature of the cell itself, and any dyeing or staining to which the cell may previously have been subjected, fluorescence emissions may also occur.

In conventional operation, photosensors located at various orientations with respect to the cell stream and the incident laser light permit detection of a set of responses for each given type of cell. Thus FIG. 1 includes an argon ion laser 101 and a helium neon laser 102, with the coherent light emitted by each being variously deflected via mirrors 103 and 104 and a lens 105 to the sensing zone of the flow channel 106. As is known in the art, the cell sample stream is carried in laminar fashion within a flowing fluid sheath, to insure that but a single cell will be illuminated in the sensing zone at a given time. Hence, as each cell is illuminated by light from the lens, interaction of the cell with the light may be sensed. As shown in FIG. 1, an extinction sensor 108 detects the amount of light blocked by the cell, and forward light scatter is detected by photosensors 109 and 110 approximately in a cone of half-angle 20°. Electrical signals generated by the sensors 108, 109 and 110 are coupled to amplifiers 120 and 121, which present electrical signals of suitable amplitude and the like for subsequent analysis and/or display.

In the apparatus of FIG. 1, light which is emitted from the cell by virtue of a fluorescence response is sensed at right angles both to the direction of cell flow and to the axis of incident light. A spherical mirror 125 and a condenser lens 107 collects this light approximately in a cone of half-angle 20°, and couples this light through an aperture 111, successively to a dichroic mirror 112 and to a second mirror 113. A first color filter 114 (e.g. to pass relatively long wavelength light such as red) conveys select light from the dichroic mirror 112 to photosensor 117 (e.g. a photomultiplier tube). A second filter 115 selectively passes light of a different color (e.g. relatively short wavelength light such as green) from the second mirror 113 to a second photosensor 116. Electrical signals from sensors 116 and 117, in the form of pulses corresponding to light from respective cells, are coupled to amplifiers 118 and 119, thereby also to produce signals which are adapted for processing.

As shown in the FIG. 1 embodiment, a sensor selector 122 generates output histograms utilizing signals from the amplifiers 118 through 121. For example, one useful form of output is a plot of amplitude of red fluorescence, from sensor 117, against amplitude of green fluorescence, from sensor 116. Such a histogram is shown at display 123, with each point on the histogram representing an individual cell. Clusters or aggregates of indicators on the histogram represent groups of cells of similar type. Quite evidently, those of ordinary skill in the art find it useful variously to generate histograms of narrow forward angle scatter versus intensity of green fluorescence, narrow forward angle scatter versus axial light extinction, and so forth.

Typically, the flow cell 106 is constructed with flat sections of quartz glass and has a specially shaped injection nozzle and funnel to insure stable laminar flow of sample and concentric sheath.

Conventionally, then, the signals generated by the photomultipliers 116 and 117 are in the form of positive pulses which have been emitted by illumination of a cell in the flow channel 106 which has been stained by a fluorescing dye. In accordance with the principles of the present invention, a photomultiplier (e.g. 116) will receive from a filter (115) a continuous fluorescent light signal, and negative pulses will be coupled to an amplifier (118) upon passage of a cell through the sensing zone of flow channel 106, which eliminates or substantially reduces the fluorescent light emitted from the sensing zone. It is preferable, then, that amplifier 118 be adapted to receive negative going, rather than positive going pulses. Such adaptation is well within the routine ability of those of ordinary skill in the art.

Various dyes or fluorescent macromolecules may be suited for the present invention. In a preferred application of the principles of the present invention, a dye is produced from fluorescein isothiocyanate conjugated to dextran (FITC-dextran) approximately 20,000 molecular weight. The large dextran molecules prevent the dye from entering the cells, and it is a further characteristic that the FITC-dextran does not adhere to the surface of the cells. A suitable concentration for a cell suspension is 0.01% to 1% FITC-dextran by weight. For such a dye, a suitable illumination source is a 488 nm. light from an argon laser, such as is conventionally included in the above described system commerically known as CYTOFLUOROGRAPH ®. Illumination of the cell suspension by the blue argon laser 101 produces a green fluorescent light which passes through dichroic mirror 112, is reflected from mirror 113 and passed through green filter 115, to be converted to electrical signals by photomultiplier tube 116.

In accordance with the principles of the present invention, which are premised on a volume exclusion technique, the fluorescent sample stream is to be larger than the cell suspended in it. Otherwise, passage of a larger cell through the optical sensing zone would result in an exclusion of but part of the total cell volume. Given a sensing zone wherein the sample stream is properly larger than the cell suspended in it, the fraction of sensing zone volume excluded by the cell may be represented in terms of the height of the laser beam intersecting the sample stream, the diameter of the sample stream, and the volume of the cell such that the exclusive volume fraction is the ratio of cell volume to the product of laser beam height and the sample stream cross sectional area. If the light intensity is uniform across the laser beam, the excluded volume fraction is directly proportional to amplitude of the fluorescent volume exclusion pulse. In the more likely event, the illuminating laser beam does not have uniform intensity across its cross section, for example employing a Gaussian intensity distribution, with greater intensity at the center and reduced intensity along the periphery. In such instance, it is preferable and more accurate to measure not only the amplitude of the fluorescence volume exclusion pulses, but furthermore to accumulate the integral of such pulses (i.e. the area under the amplitude vs. time representation of the pulse). The integral of the fluorescence volume exclusion pulse represents an averaging of fluorescence volume exclusion signal as the cell is scanned by the non-uniform laser beam. For many applications, the integral of the volume exclusion pulse is a preferable measure of cell volume.

In the event that it is desired to employ the integral of the pulse, rather than simply the amplitude, it is well within the capability of those of ordinary skill in the art that the associated amplifier circuitry such as 118 in FIG. 1 be adapted to integrate pulses presented via channel 2 from photomultiplier tube 116.

Figure 2:
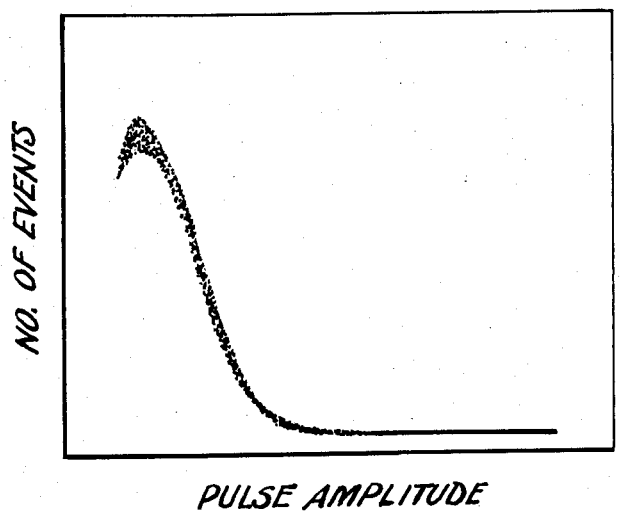
FIG. 2 shows an exemplary cell volume distribution for human erythrocytes developed in accordance with the principles of the present invention.

Typically, utilization of fluorescence volume exclusion pulses as an index of cell volume results in a rather low signal to noise ratio. For example, referring to FIG. 2, there is shown a distribution of integrated fluorescence volume exclusion pulses for human erythrocytes utilizing the FITC-dextran conjugate, as described above, as an addition to the blood. In FIG. 2, wherein the abscissa represents the integrated pulse amplitude and the ordinate represents the number of events, or cells having the corresponding integrated pulse amplitude, a sharp cutoff is exhibited at the lower end of the integrated pulse amplitude axis, which is an artifact of the electronics utilized in systems of the type exemplified in FIG. 1. By comparison, conventional wisdom holds that the actual volume distribution for human erythrocytes is a symmetric and approximately Gaussian distribution.

These observed and theoretical distribution characteristics may be quantitatively observed by defining the coefficient of variation (COV) as the ratio of standard deviation to mean. If the signals were noise free, the COV of the FIG. 2 distribution would be 0.15 to 0.2. (Noise in the signals tends to increase the COV.) For the FIG. 2 data, the actual COV is approximately 0.8. Hence, from FIG. 2 and associated analysis, the signal is seen to be quite noisy, thereby presenting some difficulties in accurately controlling the fluorescence integrating and analyzing electronics, and interpreting the data generated thereby.

In accordance with a feature of the present invention, utilization of fluorescence volume exclusion pulses as a measurement of cell volume may be enhanced significantly by utilizing an independent signal from the cell to trigger or gate the fluorescence integrating and analyzing electronics. Such independent signals may be, for example, low angle scatter at sensors 109 and 110, or wide angle scatter via mirror 112 and photomultiplier tube 117, providing that mirror 112 and filter 114 is adapted to sense scatter (e.g. blue light) as opposed to sensing fluorescence components. In fact, the data shown in FIG. 2 were obtained by triggering the fluorescence and analyzing electronics with a low angle light scattering signal obtained simultaneously with the fluorescent signal as a cell traverses the laser beam. In other words, referring to FIG. 1, detection of light at 109 and 110, which has been scattered by a cell passing through the sensing zone, is utilized via amplifier 120 to enable or gate the sensor selector 122 then to receive and process fluorescence data from amplifier 118. Alternatively, similar gating may be employed via a wide angle scatter signal from amplifier 119.

Noisy fluorescence volume exclusion signals can be also used quite precisely to measure the mean cell volume of a cell population if a sufficient number of cells is analyzed. In accordance with such an approach, well-known statistical relationships may be utilized to determine the precision of the mean of the measurement. For example, the mean integrated volume exclusion signal may be determined with a precision of 1% and a confidence level of 99%, if the signal distribution has a COV of 0.8 and if 50,000 cells are analyzed. Likewise, the mean can be determined even more precisely if more than 50,000 cells are analyzed.

It is possible that under certain conditions, spurious artifacts may be entailed, and high levels of accuracy may require compensation for these artifacts.

First, the signal may be influenced by incident or fluorescent light that is scattered or absorbed by the cell. Although such scatter and absorption generally will be minimal, their effect can nevertheless be reduced. Scatter effects can be reduced by, as nearly as possible, matching the indices of refraction of the sample and sheath fluids in the flow channel 106 with the index of refraction of the cell. Absorption effects can be minimized by judicious choice of excitation and emission light wavelengths.

Second, high accuracy determinations may be influenced by artifacts associated with disturbance of the sample stream due to the presence of the cell. If the sample stream diameter is only slightly larger than the cell, a positive polarity fluorescence pulse may follow the negative polarity fluorescence volume exclusion pulse. Generally, the following positive pulse will be larger, and the negative exclusion pulse will be smaller, as the cell diameter approaches the size of the light-flow sensing zone. In the extreme case of a very small sample stream, the fluorescent volume exclusion pulse may be negligible, while the trailing positive pulse may be rather large. Accordingly, knowledge of the sort of cells being measured, and their relative range of diameters, allows for selection of a stream size whereby trailing positive fluorescence pulses may be minimized, and the accuracy of the integration of negative fluorescence exclusion pulses will thereby be preserved. Less desirably, electronic observations and gated corrections may be employed to eliminate the undesired effect of trailing positive pulse artifacts.

It is understood that the foregoing sets forth preferred and illustrative embodiments of the principles of the present invention, but that numerous alternative embodiments will occur to those of ordinary skill in the art without departure from the spirit or scope of the present invention.

What is claimed is:

1. A method of evaluating cell volume in a sample of cells comprising the steps of:
   (a) suspending the cells of said sample in a medium including a dye which exhibits fluorescence response to select stimulation, and which is non-penetrating and substantially non-adherent to said cells;
   (b) passing said medium through an optical flow cytometry sensing zone illuminated by said select stimulation;
   (c) detecting reductions of fluorescent emissions from said sensing zone occasioned by passage of cells through said zone; and
   (d) evaluating cell volume based on the amplitude of said detected reductions of fluorescent emissions.

2. A method as described in claim 1 wherein said detecting step includes generating a pulse signal representing fluorescent emission amplitude from said zone, and said evaluating step comprises integrating said pulse signal, to produce a signal representative of mean cell volume.

3. A method as described in claim 1 and further including the step of detecting components of said select stimulation which are scattered from cells in said zone, performance of said detecting and evaluating steps being conditioned on such detection of components of said stimulation.

4. A method as described in claim 1 wherein said dye is formed of fluorescein isothiocyanate conjugated to dextran.

5. A method as described in claim 4 wherein said passing step comprises forming said suspension into a sample stream flowing through said zone, said stream being larger in diameter than said cells but sufficiently constricted to pass but one cell at a time through said zone, and illuminating said zone with focused coherent light in the blue color range.

6. A method as described in claim 4 wherein said passing step includes forming said sample into a laminar flow enclosed within a flowing carrier, wherein the optical indices of refraction of said medium and of said carrier are matched to the index of refraction of said cells.

* * * * *